United States Patent [19]
Popkova et al.

[11] Patent Number: 5,936,102
[45] Date of Patent: Aug. 10, 1999

[54] PROCESS FOR THE PREPARATION OF 2,2,3,3-TETRAFLUORO-1,4-BENZODIOXANES, NOVEL O-(2-BROMO-1,1,2,2-TETRAFLUOROETHOXY)-PHENOLS, AND NOVEL 2-BROMO-1,1,2,2-TETRAFLUOROETHOXY-CONTAINING PHENYL ETHERS

[75] Inventors: Vera Yakovlevna Popkova, Moscow, Russian Federation; Albrecht Marhold, Leverkusen, Germany

[73] Assignee: Bayer Aktiengesellschaft, Germany

[21] Appl. No.: 09/121,400

[22] Filed: Jul. 23, 1998

[30] Foreign Application Priority Data

Jul. 24, 1997 [DE] Germany .............................. 197 31 785

[51] Int. Cl.$^6$ .......................... C07C 43/20; C07C 43/29; C07D 319/16
[52] U.S. Cl. .......................... 549/362; 568/633; 568/649; 568/651; 568/652; 549/366
[58] Field of Search ...................................... 549/359, 362, 549/366; 568/633, 649

[56] References Cited

U.S. PATENT DOCUMENTS

| | | | |
|---|---|---|---|
| 4,600,787 | 7/1986 | Marhold et al. | 549/362 |
| 4,611,003 | 9/1986 | Marhold et al. . | |
| 4,737,509 | 4/1988 | Plummer | 514/386 |
| 4,886,816 | 12/1989 | Franckowiak et al. . | |
| 5,258,526 | 11/1993 | Knuppel et al. . | |
| 5,283,378 | 2/1994 | Bielefeldt et al. . | |
| 5,344,944 | 9/1994 | Franckowiak et al. . | |
| 5,378,726 | 1/1995 | Yanagi et al. . | |
| 5,463,008 | 10/1995 | Lui et al. | 549/362 |
| 5,648,316 | 7/1997 | Assmann et al. . | |

FOREIGN PATENT DOCUMENTS 0 623 609 A1  11/1994  European Pat. Off. .
3315147 A1   10/1984  Germany .

*Primary Examiner*—Johann Richter
*Assistant Examiner*—Taofiq A. Solola
*Attorney, Agent, or Firm*—Brinks Hofer Gilson & Lione

[57] ABSTRACT

The present invention is drawn to a process for preparing a 2,2,3,3-tetrafluoro-1,4-benzodioxane, by cyclocondensing a o-(2-bromo-tetrafluoroethoxy)-phenol in the presence of an acid binder.

18 Claims, No Drawings

PROCESS FOR THE PREPARATION OF 2,2,3,3-TETRAFLUORO-1,4-BENZODIOXANES, NOVEL O-(2-BROMO-1,1,2,2-TETRAFLUOROETHOXY)-PHENOLS, AND NOVEL 2-BROMO-1,1,2,2-TETRAFLUOROETHOXY-CONTAINING PHENYL ETHERS

BACKGROUND OF THE INVENTION

The present invention relates to a process for the preparation of 2,2,3,3-tetrafluoro-1,4-benzodioxanes, to novel intermediates occurring in this process, and to processes for their preparation. 2,2,3,3-Tetrafluoro-1,4-benzodioxanes are required as intermediates in the preparation of active compounds for pharmaceutics and agriculture (see, for example, DE-A37 16 652, U.S. Pat. No. 4,886,816, DE-A19 501 367, DE-A4 415 435 U.S. Pat. No. 5,648,316, and DE-A4 217 725).

A three-step process starting from pyrocatechol for the preparation of unsubstituted 2,2,3,3-tetrafluoro-1,4-benzodioxane is known from the literature. In the first step, pyrocatechol is reacted with trifluorochloroethene to give 2,2,3-trifluoro-1,4-benzo-dioxane. The latter must then be chlorinated to give 2,2,3-trifluoro-3-chloro-1,4-benzo-dioxane. In the third step, finally, a chlorine/fluorine exchange is performed. This process has a series of disadvantages. Performance of the last step is only unsatisfactory. Fluorination by means of disproportioning in the presence of antimony(V) chloride is complicated from the technical point of view and requires 50% by weight of the material to be recirculated (see DE-A 3 315 147) U.S. Pat. No. 4,600,787. Reproducibility of the alternative gas-phase reaction with hydrogen fluorine at 350° C. (see EP-A 623 609 U.S. Pat. No. 5,463,088) is poor, and its realization on an industrial scale would be extremely complicated. The corrosive media, such as the liberation of hydrogen chloride when chlorine gas is employed in the second step, and, if appropriate, the use of hydrogen fluorine in the third step, are of little advantage. Moreover, this process cannot be applied without difficulty to substituted pyrocatechols. For example, alkyl substituents on the benzene ring are also chlorinated under the chlorination conditions applied.

SUMMARY OF THE INVENTION

There has now been found a process for the preparation of 2,2,3,3-tetrafluoro,1,4-benzodioxanes of the formula

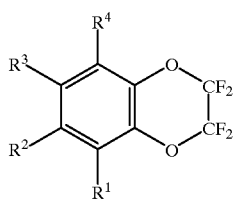

(I)

in which
$R^1$ to $R^4$ independently of one another in each case represents hydrogen, halogen or $C_1$–$C_6$-alkyl,
it also being possible for two adjacent radicals of $R^1$ to $R^4$ jointly to represent —(CH$_2$)$_3$—, —(CH$_2$)$_4$—, —(CH$_2$)$_5$— or to represent a chain —CH=CH—CH=CH— which is optionally substituted by halogen or $C_1$–$C_6$-alkyl,
and it being possible for one or two of the radicals $R^1$ to $R^4$ additionally also to represent nitro, cyano, —CO—R$^6$ or —C(OR$^7$)$_2$R$^6$, where R$^6$=hydrogen or $C_1$–$C_6$-alkyl and R$^7$=$C_1$–$C_6$-alkyl, or both radicals together=—CH$_2$CH$_2$—, —CH$_2$CH(CH$_3$)—, —CH$_2$CH(C$_2$H$_5$)— or —CH(CH$_3$)CH(CH$_3$)—, which comprises subjecting o-(2-bromo-tetrafluoroethoxy)-phenols of the formula

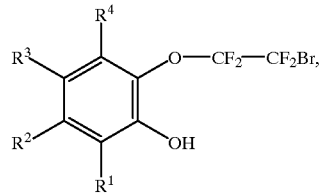

(II)

in which $R^1$ to $R^4$ have the meanings given for formula (I)
to a cyclocondensation reaction in the presence of an acid binder.

The compounds of the formula (III) are new and also subject-matter of the present invention.

There has furthermore been found a process for the preparation of the phenols of the formula (II) which comprises subjecting compounds of the formula (III)

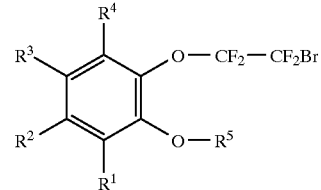

(III)

in which
$R^1$ to $R^4$ have the meanings given for formula (I) and
$R^5$ represents $C_1$–$C_6$-alkyl or benzyl
to an ether cleavage.

With the exception of 1-(2-bromo-1,1,2,2-tetrafluoroethoxy)-2-methoxy-4-nitro-benzene, whose preparation, however, has not been described in the literature (see U.S. Pat. No. 4,737,509), the compounds of the formula (III) are novel and also subject-matter of the present invention.

There has furthermore been found a process for the preparation of the compounds of the formula (III) which comprises reacting compounds of the formula (IV)

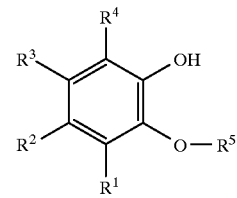

(IV)

in which $R^1$ to $R^4$ have the meanings given for formula (I) and $R^5$ the meanings given for formula (III)
with 1,2-dibromo-1,1,2,2-tetrafluoroethane in the presence of an acid binder.

DESCRIPTION OF THE INVENTION

Some of the compounds of the formula (IV) are commercially available or can be prepared by known methods or by methods analogous thereto. 1,2-Dibromo-1,1,2,2-tetrafluoroethane is commercially available as a fire-extinguishing substance.

The compounds which can be prepared in accordance with the invention are defined by formulae (I), (II) and (III), and the compounds according to the invention by formulae (II) and (III), where, however, the compound 1-(2-bromo-1,1,2,2-tetrafluoroethoxy)-2-methoxy4-nitro-benzene is excepted in the case of the formula (II).

The symbols used in formulae (I), (II), (III) and (IV) have the following preferred meanings:

$R_1$ to $R^4$ hydrogen, fluorine, chlorine, bromine or $C_1$–$C_4$-alkyl, it also being possible for two adjacent radicals of $R^1$ to $R^4$ jointly to represent —$(CH_2)_3$—, —$(CH_2)_4$—, or to represent a chain —CH=CH—CH=CH— which is optionally substituted by fluorine, chlorine, bromine or $C_1$–$C_4$-alkyl, and it being possible for one or two of the radicals $R^1$ to $R^4$ additionally also to represent nitro, cyano, —CO—$R^6$ or —C(OR$^7$)$_2$R$^6$.

$R^5$ $C_1$–$C_4$-alkyl or benzyl.

$R^6$ hydrogen or $C_1$–$C_4$-alkyl.

$R^7$ methyl, ethyl or both radicals $R^7$ together —$CH_2CH_2$— or —$CH_2CH(CH_3)$.

The symbols used in formulae (I), (II), (III) and (IV) have the following especially preferred meanings:

$R^1$ to $R^4$ hydrogen, fluorine, chlorine, bromine, methyl, ethyl, n-propyl, isopropyl, n-butyl, isobutyl, sec-butyl or tert-butyl, it also being possible for two adjacent radicals of $R^1$ to $R^4$ jointly to represent —$(CH_2)_3$—, or to represent a chain —CH=CH—CH=CH— which is optionally substituted by fluorine, chlorine, bromine, methyl, ethyl, n-propyl, isopropyl, n-butyl, isobutyl, sec-butyl or tert-butyl and it also being possible for one of the radicals $R^1$ to $R^4$ to represent nitro, cyano, —CO—$R^6$ or —C(OR$^7$)$_2$R$^6$.

$R^5$ methyl, ethyl, n-propyl, isopropyl, n-butyl, isobutyl, sec-butyl, tert-butyl or benzyl.

$R^6$ hydrogen, methyl, ethyl, n-propyl, isopropyl, n-butyl, isobutyl or tert-butyl.

$R^7$ methyl or ethyl or both radicals $R^7$ together —$CH_2CH_2$—.

The symbols used in formulae (I), (II), (III) and (IV) have the following very especially preferred meanings:

$R^1$ hydrogen.

$R^2$ hydrogen, methyl or ethyl.

$R^3$ hydrogen, methyl, ethyl, chlorine or formyl.

$R^4$ hydrogen, methyl, ethyl or formyl.

$R^2$ and $R^3$ —CH=CH—CH=CH—.

$R^5$ methyl or ethyl.

The definitions mentioned above in general or in preferred ranges can be combined with each other as desired, that is to say combinations between the individual ranges and preferred ranges are also possible.

Preferred, especially preferred and very especially preferred compounds of the formulae (I), (II), (III) and (IV) are those in which there exists a combination of the meanings termed thus above.

Hydrocarbon radicals such as alkyl can be in each case straight-chain or branched.

Optionally substituted radicals can be monosubstituted or polysubstituted, for example up to trisubstituted, it being possible for the substituents to be identical or different in the case of multiple substitutions.

Examples of suitable acid binders for the reaction of compounds of the formula (IV) with 1,2-dibromo-1,1,2,2-tetrafluoroethane are customary inorganic or organic bases. These include hydrides, hydroxides, amides, alkoxides, acetates, carbonates and hydrogen carbonates of alkali metals and alkaline earth metals, for example sodium hydride, sodium hydroxide, potassium hydroxide, ammonium hydroxide, sodium amide, lithium diisopropylamide, sodium methoxide, sodium ethoxide, potassium tert-butoxide, sodium acetate, potassium acetate, calcium acetate, ammonium acetate, sodium carbonate, potassium carbonate, ammonium carbonate, sodium hydrogen carbonate, potassium hydrogen carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) and diazabicycloundecene (DBU). Potassium carbonate is preferred.

This reaction is preferably carried out in the presence of a dituent. Suitable for this purpose are, for example, dipolar-aprotic solvents and mixtures of these. Examples which may be mentioned are: nitrites such as acetonitrile, propionitrile, n- and i-butyronitrile and benzonitrile, amides such as formamide, N,N-dimethylformamide, N,N-dimethylacetamide, N-methylformanilide, N-methylpyrrolidone and hexamethylphosphoric triamide, N-oxides such as N-methylmorpholin-N-oxide, esters such as methyl acetate, ethyl acetate or butyl acetate, sulfoxides such as dimethyl sulfoxide and sulfones such as sulfolane. Dimethyl sulfoxide is preferred.

When carrying out this reaction, the temperature can be varied within a wide range. In general, the process is carried out at 20 to 130° C., preferably at 70 to 120° C.

For example 1 to 3 mol, preferably 1.5 to 2.5 mol, of 1,2-dibromo-1,1,2,2-tetrafluoroethane, for example 1 to 6 equivalents, preferably 1 to 4 equivalents, of acid binder and for example 600 to 3000 ml, preferably 1500 to 2500 ml, of diluent may be employed per mole of compound of the formula (IV).

This reaction can be carried out under atmospheric pressure or under elevated pressure. It is advantageous to carry out the process in a sealed vessel, thus allowing a pressure of, for example, up to 10 bar to establish itself in the reaction.

In this reaction, small amounts of the corresponding reduced 1,1,2,2-tetrafluoroethyl ether (V) are formed, depending on the substituents and the reaction conditions

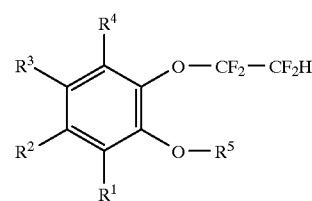

(V)

The reaction can be carried out and the reaction products can be worked up and isolated by generally customary processes. If desired, the compounds of the formulae (III) and (V) can be separated, for example by distillation or column chromatography. However, the compounds of the formulae (III) and (V) are preferably not separated, but their mixture is reacted further.

The ether cleavage of compounds of the formula (III) to give phenols of the formula (II) can be carried out by methods known per se. For example, aqueous hydrohalic acids such as hydrogen iodide, hydrogen bromide or hydrogen chloride are employed, and, if appropriate, the process is carried out in the presence of a $C_1$–$C_4$-carboxylic acid such as formic acid or acetic acid as solubilizer. The concentration of the hydrohalic acid is preferably between 20% by weight and the saturation concentration. It is also possible to employ gaseous hydrohalic acid, in which case the process is preferably carried out in an autoclave. If a benzyl ether (formula (III), $R^5$=benzyl) is employed, the ether cleavage is preferably carried out by means of catalytic hydrogenation. Examples of suitable catalysts are Raney nickel or palladium on charcoal, and examples of suitable solvents are methanol, ethanol or ethyl acetate.

If the compound of the formula (III) contains acetal or ketal substituents (one or two of the radicals $R^1$ to $R^4$=— $C(OR^7)_2R^6$), then these are also cleaved when carrying out the ether cleavage with acid and converted into the corresponding carbonyl radical of the formula —CO—$R^6$. If the target product of the synthetic sequence is a benzodioxane of the formula (I) where at least one of the radicals $R^1$ to $R^4$ is —$C(OR^7)_2R^6$, it is therefore advantageous to start from a corresponding pyrocatechol which is protected by one benzyl, of the formula (IV), where $R^5$ is benzyl, and to carry out the ether cleavage in the form of a catalytic hydrogenation. Naturally, the ketal or acetal function can also be restored, or prepared for the first time, from the carbonyl function —CO—$R^6$ when the synthesis has ended.

When carrying out the ether cleavage, the temperature can be varied within a wide range. For example, the acidic cleavage may be carried out at 30 to 150° C., preferably 50 to 140° C. The catalytic hydrogenation can be carried out, for example, at 0 to 50° C., preferably at room temperature.

When carrying out the acidic ether cleavage, the amount of acid to be used is not critical with regard to its upper limit. It is expedient to employ at least the theoretically required amount of 1 mol of hydrohalic acid per mole of the compound of the formula (III). Reactants and auxiliaries are preferably employed in those amounts which give a largely homogeneous solution during the acidic ether cleavage. It is especially advantageous to employ aqueous hydrobromic acid at a concentration of 30 to 70% by weight and acetic acid of a concentration of 80 to 100% by weight in a weight ratio of 1:1.5 to 1:3, first dissolving the compound of the formula (III) in the acetic acid and then adding the hydrobromic acid.

If a compound of the formula (III) which contains a compound of the formula (V) is employed, the result is an o-tetrafluoroethoxyphenol of the formula (VI)

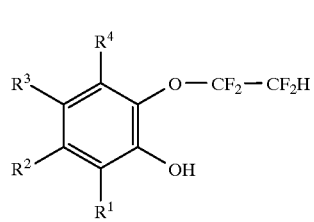

(VI)

The reaction can be carried out and the reaction products can be worked up and isolated by customary processes. If desired, compounds of the formulae (II) and (VI) can be separated, for example by distillation or column chromatography. However, the compounds of the formulae (II) and (VI) are preferably not separated, but their mixture is reacted further.

The cyclo condensation of the phenols of the formula (II) to give the benzodioxanes of the formula (I) is carried out in the presence of an acid binder. Examples of suitable acid binders are those which have been indicated further above for the reaction of compounds of the formula (IV) to give compounds of the formula (III). Preferred as acid binders for the cyclocondensation of the phenols of the formula (II) to give the benzadioxanes of the formula (I) are sodium hydroxide, potassium hydroxide, sodium methoxide and potassium methoxide.

If appropriate, this cyclocondensation reaction can be carried out in the presence of a diluent. Examples of suitable diluents are higher-boiling dipolar-aprotic solvents such as sulfones, in particular sulfolane. A diluent is preferably employed.

This cyclocondensation can be carried out for example at 80 to 180° C., preferably at 100 to 140° C.

To carry out this cyclocondensation reaction, 1 to 4 equivalents, preferably 1 to 2 equivalents, of acid binders can be employed per mole of the phenol of the formula (II), for example.

The reaction can be carried out and the reaction products can be worked up and isolated by generally customary processes.

In a preferred embodiment, a two-step sequence is performed. Firstly, the corresponding phenolate is prepared by reacting the phenol of the formula (II) with an acid binder from the series of the alkaline earth metal hydroxides and the alkali metal hydroxides, alkali metal alkoxides and alkali metal acetates at barely elevated temperature by distilling off the light component, for example water, alcohol or acetic acid, if appropriate under reduced pressure and if appropriate by adding a diluent or azeotrope former, such as toluene. If the diluent has not been added already, this is done now, and cyclocondensation is performed by elevating the temperature, during which process the resulting 2,2,3,3-tetrafluoro-1,4-benzodioxane of the formula (I) can be distilled off in most cases directly under reduced pressure. Any o-tetrafluoroethoxyphenol of the formula (VI) which may have been introduced into the reaction remains in the bottom product in the form of a phenolate.

Unless otherwise specified, all process steps are normally carried out under atmospheric pressure. However, it is also possible to carry out the process under elevated or reduced pressure.

All process steps can be carried out continuously or batchwise, in particular the cyclization reaction.

The process according to the invention also allows the direct preparation of substituted 2,2,3,3-tetrafluoro-1,4-benzodioxanes in good yields, which is beyond the prior art. This can also be carried out in a simple manner on an industrial scale and avoids corrosive media such as chlorine and hydrogen fluoride.

EXAMPLES

The percentage compositions of products and starting materials, according to GC, are based on the areas (area %) of the signals of a flame-ionization detector and are therefore generally not identical with molar or weight percentages.

Example I-1
Preparation of 2,2,3,3-tetrafluro-1,4-benzodioxane

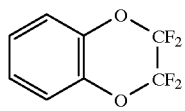

A solution of 10.16 g of 2-(2-bromo-1,1,2,2-tetrafluoroethoxy)-phenol in 20 ml of dry diethyl ether was added dropwise to a stirred suspension of 2.68 g of potassium methoxide in 20 ml of dry diethyl ether. After the exothermic reaction had subsided, diethyl ether and methanol were evaporated to dryness.

9.52 g of the resulting dry potassium salt were heated in vacuo (14 mbar) in 25 ml of dry sulfolane at 125 to 145° C., with stirring, the distillate which passed over being collected in a receiver cooled to −78° C. This gave 5.01 g (82.8% of theory) of 2,2,3,3-tetrafluoro-1,4-benzodioxane. The product was uniform as determined by gas chromatography, and the $^1$H NMR, $^{19}$F NMR and MS spectra corresponded to those of 2,2,3,3-tetrafluoro-1,4-benzodioxane prepared in accordance with DE-A 3 314 147.

Heating of the dry potassium salt was also performed continuously (addition: 27 g in the course of one hour), identical conditions being adhered to and the result per hour being 14.3 g of 2,2,3,3-tetrafluoro-1,4-benzodioxane.

Example I-2
Preparation of 2,2,3,3-tetrafluoro-1,4-benzodioxane

A solution of 2.87 g of potassium hydroxide in 10 ml of methanol was added dropwise to a solution of 9.86 g of 2-(2-bromo-1,1,2,2-tetrafluoroethoxy)-phenol in 10 ml of methanol. Methanol and water were then evaporated to dryness in vacuo. The remaining water was removed azeotropically in vacuo from the solid residue by addition of toluene and re-evaporation.

7.89 g of the resulting dry potassium salt were heated in vacuo (15 to 20 mbar) in 25 ml of dry sulfolane at 140 to 145° C., with stirring, the distillate which passed over being collected in a receiver cooled to −78° C. This gave 3.08 g (61.4% of theory) of 2,2,3,3-tetrafluoro-1,4-benzodioxane. The product was uniform as determined by gas chromatography, and the $^1$H NMR, $^{19}$F NMR and MS spectra corresponded to those of 2,2,3,3-tetrafluoro-1,4-benzodioxane prepared in accordance with DE-A 3 315 147.

Example I-3
Preparation of 6-formyl-2,2,3,3-tetrafluoro-1,4-benzodioxane

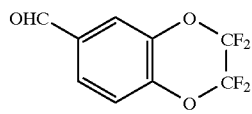

A mixture of dry potassium salts of 3-(2-bromo-1,1,2,2-tetrafluoroethoxy)-4-hydroxybenzaldehyde (85 area %) and 3-(1,1,2,2-tetrafluoroethoxy)-4-hydroxybenzaldehyde (15 area %) was prepared analogously to Example I-2, and 2.80 g thereof were heated in 20 ml of dry sulfolane at 145° C./10 mbar. This gave 1.62 g of a mixture of 13.4 area % of 6-formyl-2,2,3,3-tetrafluoro-1,4-benzodioxane (12.7% of theory) and 86.6 area % of sulfolane (GC analysis). The desired product, boiled at 100° C./20 mbar, was obtained in pure form by distillation. It corresponded to 6-formyl-2,2,3,3-tetrafluoro-1,4-benzodioxane obtained in accordance with DE-A 3 716 652.

Example I-4
Preparation of 6-chloro-2,2,3,3-tetrafluoro-1,4-benzodioxane

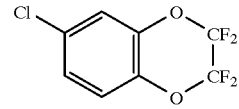

10.0 g of a mixture of 77 area % of 1-hydroxy-2-(2-bromo-1,1,2,2-tetrafluoroethoxy)-4-chlorobenzene and 23 area % of 1-hydroxy-2-(1,1,2,2-tetrafluoroethoxy)-4-chlorobenzene were stirred for 9 hours at 120° C. in 30 nil of sulfolane together with 3.48 g of potassium hydroxide. The reaction mixture was then cooled to 20° C., and the products which distilled over at 0.3 mbar and 20 to 60° C. were collected in a receiver cooled to −78° C. This gave 2.56 g of a mixture of 94.5 area % of 6-chloro-2,2,3,3-tetrafluoro-1,4-benzodioxane (41.9% of theory) and 5.5 area % of 6-chloro-2,3,3-trifluoro-1,4-benzodioxane (GC, $^1$H NMR, $^{19}$F NMR and GC-MS analysis). The desired product, which boiled at 75° C./238 mbar, was obtained in pure form by distillation.

| C/H analysis [%]: | C | H |
|---|---|---|
| calc. for $C_8H_3O_2ClF_4$: | 39.61 | 1.247 |
| found: | 39.6 | 1.3 |

Example I-5
Preparation of 2,2,3,3-tetrafluoro-6-methyl-1,4-benzodioxane

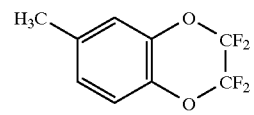

7.0 g of a mixture of 83 area % of 4-(2-bromo-1,1,2,2-tetrafluoroethoxy)-1-methyl-3-hydroxybenzene and 17 area % of 4-(1,1,2,2-tetrafluoroethoxy)-1-methyl-3-hydroxybenzene were stirred for 30 hours at 120° C. in 30 ml of sulfolane together with 1.9 g of sodium hydroxide. The reaction mixture was then cooled to 20° C., and the products which distilled over at 0.3 mbar and 20 to 60° C. were collected in a receiver cooled to −78° C. This gave 2.5 g of a mixture of 90 area % of 2,2,3,3-tetrafluoro-6-methyl-1,4-benzodioxane (52.8% of theory) and 10 area % of 2,2,3-trifluoro-6-methyl-1,4-benzodioxane (GC, $^1$H NMR, $^{19}$F NMR and GC-MS analysis). The desired product, which boiled at 98° C./238 mbar, was obtained in pure form by distillation.

| C/H analysis [%]: | C | H |
|---|---|---|
| calc. for $C_9H_6O_2F_4$: | 48.66 | 2.72 |
| found: | 49.2 | 2.9 |

The examples described above and other examples which were carried out analogously to these are compiled in Table I.

TABLE I

| Ex. No. | Prepared compound of the formula (I) | *)Proportion (II):(VI) | Reaction conditions | Physical data | Yield [% of theory] |
|---|---|---|---|---|---|
| I-1 | benzo-1,4-dioxine with $CF_2$–$CF_2$ bridge | 100:0 | dry K salt ($KOCH_3$), sulfolane, 125–145° C. | b.p.: 145° C. | 82.8 |
| I-2 | benzo-1,4-dioxine with $CF_2$–$CF_2$ bridge | 100:0 | dry K salt (KOH), sulfolane, 140–145° C. | b.p.: 145° C. | 61.4 |
| I-3 | OHC-substituted benzo-1,4-dioxine with $CF_2$–$CF_2$ bridge | 85:15 | dry K salt (KOH), sulfolane, 140–145° C. | b.p.: 100° C./20 mbar | 12.7 |
| I-4 | Cl-substituted benzo-1,4-dioxine with $CF_2$–$CF_2$ bridge | 77:23 | KOH, sulfolane, 120° C., 9 h | b.p.: 75° C./238 mbar | 41.9 |
| I-5 | $H_3C$-substituted benzo-1,4-dioxine with $CF_2$–$CF_2$ bridge | 83:17 | NaOH, sulfolane, 120° C., 30 h | b.p.: 98° C./238 mbar | 52.8 |
| I-6 | Cl-substituted benzo-1,4-dioxine with $CF_2$–$CF_2$ bridge | 89:11 | dry K salt ($KOCH_3$), sulfolane, 90–135° C. | b.p.: 75° C./238 mbar | 86.9 |
| I-7 | $H_3C$-substituted benzo-1,4-dioxine with $CF_2$–$CF_2$ bridge | 60:40 | dry K salt ($KOCH_3$), sulfolane, 120–145° C. | b.p.: 98° C./238 mbar | 99.9 |
| I-8 | naphtho-1,4-dioxine with $CF_2$–$CF_2$ bridge | 100:0 | dry K salt ($KOCH_3$), sulfolane, 120–160° C.**) | m.p.: 93–94° C. | 69.1 |

*)area %
**)The solidified distillate obtained after the reaction was washed with water and filtered, giving pure (I-8).

Example II-1
Preparation of 2-(2-bromo-1,1,2,2-tetrafluoroethoxy)-phenol

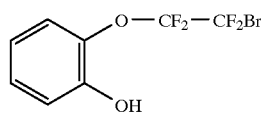

A solution of 54.42 g of 1-(2-bromo-1,1,2,2-tetrafluoroethoxy)-2-methoxybenzene in 500 ml of an acid mixture of acetic acid (96% by weight)/hydrobromic acid (48% by weight) 2.5:1 was stirred for 43 hours under reflux, the completeness of the reaction being monitored by gas chromatography (GC). The reaction mixture was then cooled to 20° C. and poured into water. The organic phase was separated off and the aqueous phase was extracted twice with dichloromethane. The extracts were added to the organic phase, and the mixture was dried over magnesium sulfate and evaporated in vacuo. Distillation of the residue gave 43.55 g (83.9% of theory) of 2-(2-bromo-1,1,2,2-tetrafluoroethoxy)-phenol of boiling point 84° C./20 mbar.

| C/H analysis [%]: | C | H |
|---|---|---|
| calc. for $C_8H_5O_2BrF_4$: | 33.24 | 1.74 |
| found: | 33.4 | 1.7 |

Example II-2 preparation of 2-(2-bromo-1,1,2,2-tetrafluoroethoxy)-3-hydroxynaphtalene and 2-(1,1,2,2-tetrafluorethoxy)-3-hydoxynaphthalene

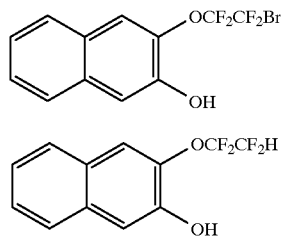

2.68 g of a mixture of 50 area % of 2-(2-bromo-1,1,2,2-tetrafluoroethoxy)-3-methoxy-naphthalene and 50 area % of 2-(1,1,2,2-tetrafluoroethoxy)-3-methoxynaphthalene were stirred for 30 hours at 120° C. in 65 ml of a solution of acetic acid (96% by weight) and hydrobromic acid (48% by weight) in a volumetric ratio of 2.5:1, during which process completeness of the reaction was monitored by gas chromatography (GC). The reaction mixture was then cooled to 20° C., poured into water and extracted with dichloromethane. The combined organic phases were dried over magnesium sulfate. The solvent was evaporated in vacuo and the residue of 1.60 g, which was composed of 63 area % of 2-(2-bromo-1,1,2,2-tetrafluoroethoxy)-3-hydroxynaphthalene and 37 area % of 2-(1,1,2,2-tetrafluoroethoxy)-3-hydroxynaphthalene (GC analysis), was separated by column chromatography on 97 g of silica gel using hexane/dichloromethane 1:1.9 as eluent. This gave 0.71 g (55.5% of theory) of the bromine-containing compound of melting point 67–68° C. and 0.532 g (42% of theory) of the bromine-free compound of melting point 70–71° C. Samples for analysis were obtained by sublimation at 60° C./10 mbar.

| C/H analysis [%]: | C | H |
|---|---|---|
| bromine-containing compound: | | |
| calc. for $C_{12}H_7O_2BrF_4$: | 42.50 | 2.08 |
| found: | 42.4 | 2.1 |
| bromine-free compound: | | |
| calc. for $C_{12}H_8O_2F_4$: | 55.39 | 3.10 |
| found: | 55.2 | 3.2 |

The examples described above and other examples which were carried out analogously to these are compiled in Table II.

TABLE II

| Ex. No. | Prepared compound of the formula (II) | Prepared compound of the formula (VI) | Proportion* (III):(V) | Reaction conditions | B.p.: [°C.]/[mbar] | Proportions* (II):(VI) | Yield of (II) [% of theory] |
|---|---|---|---|---|---|---|---|
| II-1 | 2-(OCF$_2$CF$_2$Br)phenol | 2-(OCF$_2$CF$_2$H)phenol | 100:0 | HBr (48% strength)/CH$_3$COOH (96%) 110–120° C.; 43 h | 84°/20 | 100:0 | 83.9 |
| II-2 | 3-(OCF$_2$CF$_2$Br)-2-naphthol | 3-(OCF$_2$CF$_2$H)-2-naphthol | 50:50 | HBr (48% strength)/CH$_3$COOH (96%) 120° C.; 26 h | m.p.: 67–68° C. (II); 70–71° C. (VI) | 63:37 | 55.5 |
| II-3 | 2-(OCF$_2$CF$_2$Br)phenol | 2-(OCF$_2$CF$_2$H)phenol | 75:25 | HBr (48% strength); 120° C.; 6 d | 75–80°/14 | 80:20 | 51 |
| II-4 | 2-(OCF$_2$CF$_2$Br)phenol | 2-(OCF$_2$CF$_2$H)phenol | 79:21 | HBr (48% strength)/CH$_3$COOH (96%) 110–120° C.; 20 h | 75–80°/14 | 81:19 | 72 |
| II-5 | 2-(OCF$_2$CF$_2$Br)phenol | 2-(OCF$_2$CF$_2$H)phenol | 63:37 | HBr (48% strength)/CH$_3$COOH (96%) 110–120° C.; 24 h | 70–80°/14 | 63:37 | 41.5 |

TABLE II-continued

| Ex. No. | Prepared compound of the formula (II) | Prepared compound of the formula (VI) | Proportion* (III):(V) | Reaction conditions | B.p.: [C.]/[mbar] | Proportions* (II):(VI) | Yield of (II) [% of theory] |
|---|---|---|---|---|---|---|---|
| II-6 | 2-(OCF$_2$CF$_2$Br)-phenol | 2-(OCF$_2$CF$_2$H)-phenol | 75:25 | HCl (37% strength)/ CH$_3$COOH (96%) 110–120° C.; 30 h** | 75–80°/14 | 79:21 | 72 |
| II-7 | 4-Cl-2-(OCF$_2$CF$_2$Br)-phenol | 4-Cl-2-(OCF$_2$CF$_2$H)-phenol | 78:22 | HBr (48% strength)/ CH$_3$COOH (96%) 120° C.; 46 h | 112–118°/25 | 83:17 | 76 |
| II-8 | 4-CH$_3$-2-(OCF$_2$CF$_2$Br)-phenol | 4-CH$_3$-2-(OCF$_2$CF$_2$H)-phenol | 71:29 | HBr (48% strength)/ CH$_3$COOH (96%) 120° C.; 32 h | 102–110°/0.15 | 75:25 | 77 |
| II-9 | 4-CHO-2-(OCF$_2$CF$_2$Br)-phenol | 4-CHO-2-(OCF$_2$CF$_2$H)-phenol | 83:17 | HBr (48% strength)/ CH$_3$COOH (96%) 110–120° C. | 105–110°/0.15; m.p.: 109–109.5° C. (II); 89° C. (VI) | 86:14 | 68.0 |

*)area %

***)Benzyl chloride was removed by washing the residue with sodium hydroxide solution, and extraction with dichloromethane. The subsequent acidification of the aqueous phase with hydrochloric acid and then the extraction with dichloromethane, the drying of the organic layer over magnesium sulfate and the evaporation of solvent gave compounds (II) and (VI)

Example III-1
Preparation of 2-(2-bromo-1,1,2,2-tetrafluoroethoxy)-anisole

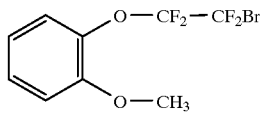

124.8 g of 1,2-dibromotetrafluoroethane were added dropwise under nitrogen to a stirred mixture of 30 g of guaiacol, 50 g of anhydrous potassium carbonate and 450 ml of dry dimethyl sulfoxide (DMSO). The mixture was then heated at 100° C. and stirred at this temperature for 24 hours. The reaction mixture was then cooled to 20° C. and poured into water. The organic phase was separated off and the aqueous phase extracted twice using dichloromethane. The extracts were added to the organic phase and the mixture was dried over magnesium sulfate. The solvent was then evaporated in vacuo and the residue was distilled. This gave 51.0 g of a mixture of 83 area % of 1-(2-bromo-1,1,2,2-tetrafluoroethoxy)-2-methoxybenzene (58.2% of theory) and 17 area % of 1-(1,1,2,2-tetrafluoroethoxy)-2-methoxybenzene (GC, $^1$H NRM and $^{19}$F NMR analysis), distilling over at 80–98° C./14 mbar. The desired product was obtained in pure form by fractional distillation over a longer packed column.

| B. p.: 80–82° C./10 mbar | | |
|---|---|---|
| C/H analysis [%]: | C | H |
| calc. for C$_9$H$_7$O$_2$BrF$_4$: | 35.67 | 2.33 |
| found: | 35.8 | 2.3 |

Example III-2
Preparation of 2-(2-bromo-1,1,2,2-tetrafluoroethoxy)-anisole 30.0 g of guaiacol, 70.0 g of 1,2-dibromotetrafluoroethane, 50.0 g of anhydrous potassium carbonate and 450 ml of dry DMSO were introduced into a stirred autoclave made of stainless steel. After the autoclave had been flushed with argon, it was sealed and subsequently heated to 100° C. After the reaction mixture had been stirred at this temperature for 24 hours, it was cooled to 20° C., poured into water and extracted with dichloromethane. The combined extracts were dried over magnesium sulfate. The dichloromethane was then evaporated in vacuo and the residue was distilled. 62.3 g of a mixture of 70 area % of 1-(2-bromo-1,1,2,2-tetrafluoroethoxy)-2-methoxybenzene (59.2% of theory) and 30 area % of 1-(1,1,2,2-tetrafluoroethoxy)-2-methoxybenzene (GC analysis) were obtained, distilling over at 80–95° C./14 mbar.

Example III-3
Preparation of 2-(2-bromro-1,1,2,2-tetrafluoroethoxy)-3-methoxynaphthalene and 2-(1,1,2,2-tetrafluoroethoxy)-3-methoxynaphthelene

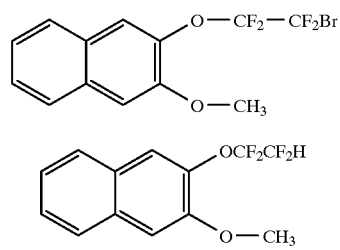

6.0 g of 3-methoxy-2-naphthol, 21.75 g of 1,2-dibromotetrafluoroethane and 5.0 g of anhydrous potassium carbonate were reacted for 66 hours at 100° C. in 400 ml of dry DMSO analogously to Example III-1. After the reaction, the solvent was evaporated in vacuo (67° C./10 mbar). The residue was combined with water and the mixture was extracted with dichloromethane. The organic phase was separated off, dried over magnesium sulfate and evaporated to dryness. The crude product (10.0 g), composed of in each case 50% by weight of 2-(2-bromo-1,1,2,2-tetrafluoroethoxy)-3-methoxy-naphthalene and 2-(1,1,2,2-tetrafluoroethoxy)-3-methoxynaphthalene (GC, $^1$H NMR and $^{19}$F NMR analysis), was separated by column chromatography on 360 g of silica gel (eluent: hexane/dichloromethane 10:3). This gave 2.6 g (21.4% of theory) of the desired bromine-containing product, 1.7 g (18 area % of theory) of the corresponding bromine-free compound and 2.7 g of a 1:1 mixture (GC analysis). Thus, the total yields of bromine-containing and bromine-free compound were approximately in each case 33% of theory.

B.p. (bromine-containing compound): 92° C./0.08 mbar

B.p. (bromine-free compound): 82° C./0.1 mbar

The examples described above and other examples which were carried out analogously to these are compiled in Table III.

TABLE III

| Ex. No. | Prepared compound of the formula (III) | Prepared compound of the formula (V) | Reaction conditions | Physical data | Proportion*) (III):(V) | Yield (III) [% of theory] |
|---|---|---|---|---|---|---|
| III-1 | (structure: OCF$_2$CF$_2$Br, O—CH$_3$) | (structure: OCF$_2$CF$_2$H, O—CH$_3$) | DMSO, K$_2$CO$_3$ 100° C.; 24 h | B.p.: 80–82°C./ 10 mbar (III) | 83:17 | 58.2 |
| III-2 | (structure: OCF$_2$CF$_2$Br, O—CH$_3$) | (structure: OCF$_2$CF$_2$H, O—CH$_3$) | DMSO, K$_2$CO$_3$ 100° C.; 24 h; autoclave | B.p.: 80–95° C./ 14 mbar | 70:30 | 59.2 |

TABLE III-continued

| Ex. No. | Prepared compound of the formula (III) | Prepared compound of the formula (V) | Reaction conditions | Physical data | Proportion*) (III):(V) | Yield (III) [% of theory] |
|---|---|---|---|---|---|---|
| III-3 | 3-methoxy-2-(OCF$_2$CF$_2$Br)naphthalene | 3-methoxy-2-(OCF$_2$CF$_2$H)naphthalene | DMSO, K$_2$CO$_3$ 100° C.; 66 h | B.p.: 92° C./0.08 mbar (III); 82° C./0.1 mbar (V) | 50:50 | 33 |
| III-4 | 2-(OCF$_2$CF$_2$Br)-1-(OCH(CH$_3$)CH$_3$... i.e. O—CHCH$_3$ with CH$_3$)benzene | corresponding OCF$_2$CF$_2$H | DMSO, K$_2$CO$_3$ 70–100° C.; 22 h | B.p.: 100–112° C./18 mbar | 81:19 | 41.0 |
| III-5 | 2-(OCF$_2$CF$_2$Br)-1-(OCH$_2$Ph)benzene | corresponding OCF$_2$CF$_2$H | DMSO, K$_2$CO$_3$ 70–110° C.; 22 h | B.p.: 112–119° C./0.13 mbar | 80:20 | 40 |
| III-6 | 4-chloro-2-(OCF$_2$CF$_2$Br)-1-methoxybenzene | corresponding OCF$_2$CF$_2$H | DMSO, K$_2$CO$_3$ 100° C.; 24 h | B.p.: 90–112° C./12 mbar | 82:18 | 58.2 |
| III-7 | 4-methyl-2-methoxy-1-(OCF$_2$CF$_2$Br)benzene | corresponding OCF$_2$CF$_2$H | DMSO, K$_2$CO$_3$ 100° C.; 24 h | B.p.: 90–105° C./10 mbar | 75:25 | 48.6 |
| III-8 | 4-formyl-2-(OCF$_2$CF$_2$Br)-1-methoxybenzene | corresponding OCF$_2$CF$_2$H | DMSO, K$_2$CO$_3$ 100–110° C.; 30 h | B.p.: 98–105° C./0.1 mbar | 88:12 | 38 (at a reaction rate of 78%) |
| III-9 | 2-formyl-6-methoxy-1-(OCF$_2$CF$_2$Br)benzene | corresponding OCF$_2$CF$_2$H | DMSO, K$_2$CO$_3$ 100° C.; 24 h | B.p.: 100–105° C./3 mbar | 67:33 | 6.1 |

*)Area %

What is claimed is:

1. A process for preparing a compound of the formula (I):

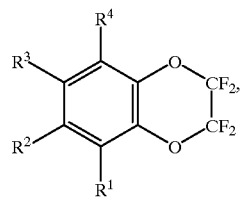

(I)

where $R^1$, $R^2$, $R^3$, and $R^4$ are each independently hydrogen, halogen or $C_{1-6}$-alkyl, or where two adjacent radicals $R^1$ to $R^4$ together form a group of the formula —(CH$_2$)$_3$—, —(CH$_2$)$_4$—, or —(CH$_2$)$_5$— or a group of the formula —CH=CH—CH=CH— which is unsubstituted or substituted by halogen or $C_{1-6}$-alkyl, or where one or two of the radicals $R^1$ to $R^4$ may be nitro, cyano, —CO—$R^6$ or —C(OR$^7$)$_2$R$^6$, where $R^6$ is hydrogen or $C_{1-6}$-alkyl and $R^7$ is $C_{1-6}$-alkyl, or where $R^6$ and $R^7$ together form a group of the formula —CH$_2$CH$_2$—, —CH$_2$CH(CH$_3$)—, —CH$_2$CH(C$_2$H$_5$)— or —CH(CH$_3$)CH(CH$_3$)—;

which comprises the steps of:

(a) reacting a compound of the formula (IV):

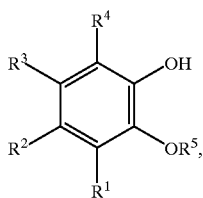
(IV)

wherein $R^1$ to $R^4$ are as above; and $R^5$ is $C_{1-6}$-alkyl or benzyl;
with 1,2-dibromo-1,1,2,2-tetrafluoroethane in the presence of an acid binder to obtain a compound of the formula (III);

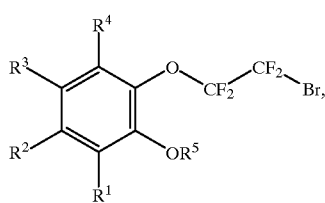
(III)

wherein $R^1$ to $R^5$ are as above;
(b) subjecting said compound of the formula (III) to an ether cleavage to obtain a compound of the formula (II)

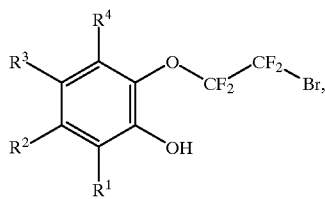
(II)

wherein $R^1$ to $R^4$ are as above; and
(c) cyclocondensing the compound of the formula (II) in the presence of an acid binder, optionally in the presence of a solvent, to obtain the compound of formula (I).

2. The process of claim 1, wherein $R^1$ to $R^4$ are each independently hydrogen, fluorine, chlorine, bromine or $C_{1-4}$-alkyl; or
where two adjacent radicals $R^1$ to $R^4$ together form a group of the formula —$(CH_2)_3$—, —$(CH_2)_4$—, or —$(CH_2)_5$— or a group of the formula —CH=CH—CH=CH— which is unsubstituted or substituted by halogen or $C_{1-6}$-alkyl, or
where one or two of the radicals $R^1$ to $R^4$ may be nitro, cyano, —CO—$R^6$ or —C(O$R^7$)$_2R^6$, where $R^6$ is hydrogen or $C_{1-6}$-alkyl and $R^7$ is $C_{1-6}$-alkyl, or where $R^6$ and $R^7$ together form a group of the formula —$CH_2CH_2$—, —$CH_2CH(CH_3)$—, —$CH_2CH(C_2H_5)$— or —CH($CH_3$)CH($CH_3$)—.

3. The process of claim 1, wherein said acid binder is an inorganic or organic base.

4. The process of claim 3, wherein said inorganic or organic base is selected from the group consisting of hydrides, hydroxides, amides, alkoxides, acetates, carbonates and hydrogen carbonates of alkali metals and alkaline earth metals, and tertiary amines.

5. The process of claim 1, wherein said acid binder is potassium carbonate.

6. The process of claim 1, wherein said cyclocondensing is conducted in the presence of a solvent.

7. The process of claim 6, wherein said solvent is a dipolar or aprotic solvent or mixture thereof.

8. The process of claim 6, wherein said solvent is dimethylsulfoxide.

9. The process of claim 6, wherein 600 to 3000 mL of solvent are employed per mole of compound of the formula (IV).

10. The process of claim 9, wherein 1500 to 2500 mL of solvent are employed per mole of compound of the formula (IV).

11. The process of claim 1, wherein said cyclocondensing is conducted at 20 to 130° C.

12. The process of claim 1, wherein said cyclocondensing is conducted at 70 to 120° C.

13. The process of claim 1, wherein 1 to 3 mol of 1,2-dibromo-1,1,2,2-tetrafluoroethane is employed per mole of compound of the formula (IV).

14. The process of claim 13, wherein 1.5 to 1.5 mol of 1,2-dibromo-1,1,2,2-tetrafluoroethane is employed per mole of compound of the formula (IV).

15. The process of claim 1, wherein 1 to 6 equivalents of acid binder is employed per mole of compound of the formula (IV).

16. The process of claim 15, wherein 1 to 4 equivalents of acid binder is employed per mole of compound of the formula (IV).

17. The process of claim 1, wherein said cyclocondensing is conducted under atmospheric or elevated pressure.

18. The process of claim 1, wherein said cyclocondensing is conducted at a pressure of up to 10 bar.

* * * * *